United States Patent [19]
Gadsby et al.

[11] Patent Number: 4,852,571
[45] Date of Patent: Aug. 1, 1989

[54] DISPOSABLE BIOPOTENTIAL ELECTRODE

[75] Inventors: Peter D. Gadsby; Martin R. Moore, both of Cedarburg; Denis E. Olson, Brookfield; Barry M. Scott, West Bend, all of Wis.

[73] Assignee: Marquette Electronics, Milwaukee, Wis.

[21] Appl. No.: 92,440

[22] Filed: Sep. 3, 1987

[51] Int. Cl.$^4$ .............................................. A61B 5/04
[52] U.S. Cl. .................................................. 128/640
[58] Field of Search ............... 128/639, 640, 641, 798, 128/802, 803

[56] References Cited

U.S. PATENT DOCUMENTS

| | | | |
|---|---|---|---|
| 3,998,215 | 12/1976 | Anderson et al. | 128/641 |
| 4,125,110 | 11/1978 | Hymes | 128/641 |
| 4,166,453 | 9/1979 | McClelland | 128/639 |
| 4,270,543 | 6/1981 | Tabuchi et al. | 128/64 D |
| 4,362,165 | 12/1982 | Carmon et al. | 128/640 |
| 4,365,634 | 12/1982 | Bare et al. | 128/640 |
| 4,377,170 | 3/1983 | Carim | 128/639 |
| 4,422,461 | 12/1983 | Glumac | 128/798 |
| 4,524,087 | 6/1985 | Engel | 128/798 X |
| 4,543,958 | 10/1985 | Cartmell | 128/640 |
| 4,556,065 | 12/1985 | Hoffman | 128/639 |
| 4,570,637 | 2/1986 | Gomes et al. | 128/639 |
| 4,640,289 | 2/1987 | Graighead | 128/639 |
| 4,643,193 | 2/1987 | DeMarzo | 128/639 |
| 4,694,835 | 9/1987 | Strand | 128/640 |

FOREIGN PATENT DOCUMENTS

| | | | |
|---|---|---|---|
| 0050342 | 4/1980 | Japan | 128/639 |
| 2179555 | 3/1987 | United Kingdom | 128/639 |

Primary Examiner—Lee S. Cohen
Attorney, Agent, or Firm—Andrus, Sceales, Starke & Sawall

[57] ABSTRACT

A disposable, biopotential electrode has a base sheet of plastic or other material. A layer of carbon is applied to the base sheet. A layer of silver/silver chloride is applied to the carbon layer. An ionically conductive adhesive is applied to the silver/silver chloride layer.

15 Claims, 1 Drawing Sheet

DISPOSABLE BIOPOTENTIAL ELECTRODE

BACKGROUND OF THE INVENTION

The present invention relates to disposable, biopotential electrodes.

Certain physiological phenomena of the body produce electrical potentials on the skin. The electrical data associated with the physiological functioning of the heart typifies such potentials. The electrical activity of the brain is another example. In order to obtain such data, it is necessary to attach electrodes to the skin of the patient. A plurality of electrodes are usually employed to measure electric potentials between a number of points on the body.

In the past, belts, or more commonly, suction bulbs were used to hold electrodes, such as electrocardiographic electrodes, on the skin. Belts are awkward to use. An electrolytic paste must be used with suction electrodes to improve the electrical connection and the suction seal. The reuse of such electrodes presents a possiblity for the transmission of disease.

As a result, disposable electrodes have been developed. An early type of disposable electrode was in the form of an adhesive pad with the male portion of a snap fastener extending through the center of the pad. A sponge, saturated with electrolyte, was placed over the fastener. A carrier covered the pad and sponge.

In use, the carrier was removed and the electrode applied to the skin with the adhesive pad holding the electrode on the skin. The lead cables for the electrocardiograph contained a mating part of the snap fastener for connection purposes. After use, the electrode was removed from the skin and discarded.

U.S. Pat. Nos. 3,834,373; 3,923,042; 3,976,055; and 3,993,049 generally show electrodes of this type.

While possessign advantages over suction electrodes, electrodes of the above described type were relatively expensive for a disposable product. Additionally, the electrolyte tended to dry out during storage, limiting the shelf life of the product.

Further development of disposable electrodes has resulted in those generally formed with a foil or film-like electrical conductor having various electrolytic and adhesive layers laminated thereon. A plastic backing sheet may be used to support the foil or film conductor. A connector extending from the foil or film is used to connect the electrode to the electrocardiograph. See, for example U.S. Pat. No. 4,125,110 to Hymes. See also U.S. Pat. Nos. 4,365,634 to Ober, et al; 4,524,087 to Engel; and 4,543,958.

However, the construction of these electrodes is such that they have difficulty in complying with all standards established by governmental regulation or industry groups for such electrodes. These standards contain certain specifications for the electrical properties of such electrodes including DC offset, AC impedance, electrical noise, bias tolerance, and defibrillation recovery. The current specification for the defibrillation recovery characteristics of a disposable electrode, as promulgated by the Association for the Advancement of Medical Instrumentation, is both important and difficult for existing electrodes of the foregoing type to meet. The specification describes certain time related, electrical dissipation properties of the electrode following the repeated electrical shock of defibrillation. If recovery time is not sufficiently quick, there will be an inordinate delay in obtaining electrocardiographic data following defibrillation. The absence of such data can be detrimental to the patient. The specification also limits the voltage that can appear on the electrode immediately following defibrillation, as well as the resultant change in voltage on the electrode over time as the electrode depolarizes.

Additionally, the cost of electrodes of this type has been greater than that desired for a disposable device.

SUMMARY OF THE PRESENT INVENTION

It is, therefore, the object of the present invention to provide an improved disposable, biopotential electrode.

It is a further object of the present invention to provde such an electrode suitable for electrocardiographic use having improved defibrillation recovery properties that meet or exceed current standards with respect to same.

It is a further object of the present invention to provde a disposable, biopotential electrode that is economical in manufacture and use.

The disposable, biopotential electrode of the present invention utilizes a base or backing sheet formed of suitable plastic material. A layer of electrically conductive carbon and/or graphite is applied to the backing sheet. A layer of silver/silver chloride is applied to the carbon layer. An ionically conductive synthetic adhesive layer is applied to the silver/silver chloride layer. A tab in the backing sheet that contains the carbon and/or silver/silver chloride layers, but not the adhesive, is provided in the electrode for connection to appropriate instrumentation.

DESCRIPTION OF THE DRAWING

The invention will be further appreciated by reference to the following detailed description, taken in conjunction with the drawing. In the drawing.

DETAILED DESCRIPTION OF THE PREFERRED EMBODIMENT

Figure 1:
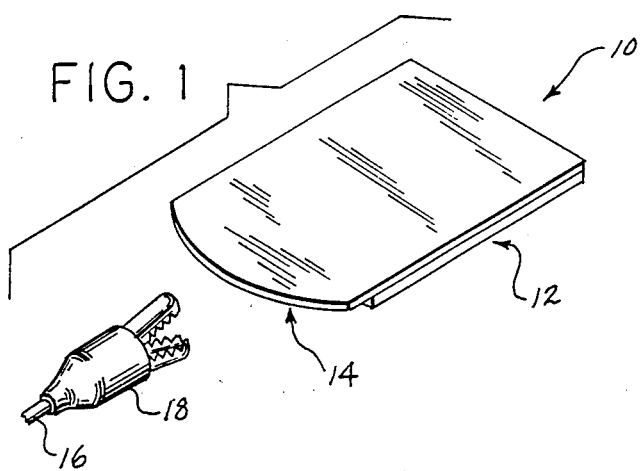
FIG. 1 is a perspective view of the improved electrode of the present invention.

In FIG. 1, the electrode of the present invention is identified by the numeral 10. The electrode shown in FIG. 1 is suitable for electrocardiographic purposes. The electrode is sheet-like in form and may have the generally rectangular shape shown in the figures, or a circular, square or other desired shape. Electrode 10 has a main portion 12 that is fastened to the patient to obtain electrocardiographic data and a tab 14 that permits connection of lead cable 16 from the electrocardiograph, as by clip 18.

Figure 2:
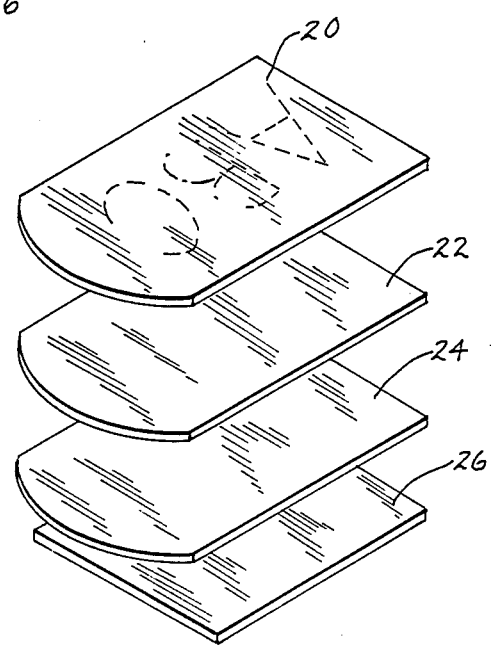
FIG. 2 is an exploded, perspective view of the electrode.

Electrode 10 is shown in detail in FIG. 2. Electrode 10 includes a base sheet 20 forming the upper element of the electrode. Sheet 20 may be formed of a plastic material of suitable composition, dimensional stability, and thickness. For example, base sheet 20 may comprise a sheet of copolyester plastic, 5 mils in thickness. The upper surface of sheet 20 may contain printed material, such as instructions or labeling. If sheet 20 is formed of a clear material, the printing may be applied to the lower surface of sheet 20.

A layer 22 of electrically conductive carbon and/or graphite is applied to the lower surface of sheet 20. Layer 22 may be applied to sheet 20 as an ink, i.e. carbon and/or graphite contained in an appropriate binder. Or, layer 22 may comprise a plastic film having the carbon and/or graphite embedded therein, the film being bonded to sheet 20. A layer 24 of silver/silver chloride lies below layer 22 when the electrode is oriented as in FIG. 2. Such a layer may comprise finely ground metallic silver having the silver chloride dispersed therein. Layer 24 is typically applied to layer 22 as an ink with the silver/silver chloride carried in an appropriate binder. Or, silver may be applied to layer 22, and the silver chloridized with an appropriate chloridizing agent, such as a hypochlorite, after application.

Silver/silver chloride is recognized to have excellent electrical properties and such a layer also provides the rapid defibrillation recovery characteristic to the electrode of the present invention. The electrically conductive properties provided by the carbon and/or graphite layer 22 reduces the cost of the more expensive silver/silver chloride layer by reducing the thickness of the silver/silver chloride ink needed to produce desired electrical properties and satisfactory operation of the electrode.

An ionically conductive, synthetic adhesive layer 26 is applied to silver/silver chloride layer 24. Adhesive layer 26 is not applied to tab 14 while silver/silver chloride layer 24 and/or carbon and/or graphite layer 22 is applied to tab 14.

Figure 3:
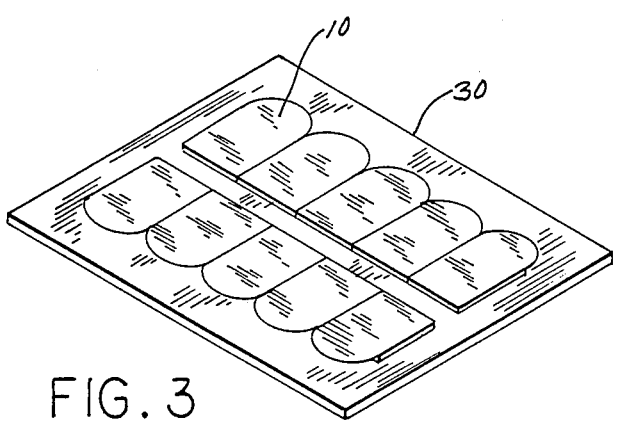
FIG. 3 is a perspective view of a plurality of electrodes on a backing sheet.

The electrodes so formed are placed on a sheet 30 for packaging and storage, as shown in FIG. 3. Sheet 30 has appropriate properties or a parting film that permits electrodes to be peeled off for use.

In use, the electrodes 10 are peeled off backing sheet 30 and applied to the skin of the patient at the appropriate locations. A lead cable 16 is fastened to each electrode 10 by clip 18 applied to tab 14. Clip 18 engages the conductive layer 24 and/or 22.

The electrical data, such as electrocardiographic information, is then obtained from the patient and provided to the instrumentation through lead cable 16. When the desired electrocardiographic data has been obtained, clip 18 is disconnected from tab 14. Electrodes 10 are then removed from the skin of the patient and discarded.

Figure 4:
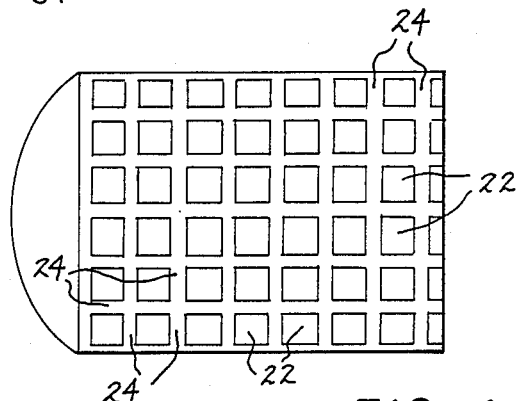
FIGS. 4 and 5 are plan views showing patterns of the layer of silver/silver chloride and carbon ink in the electrode.
Figure 5:
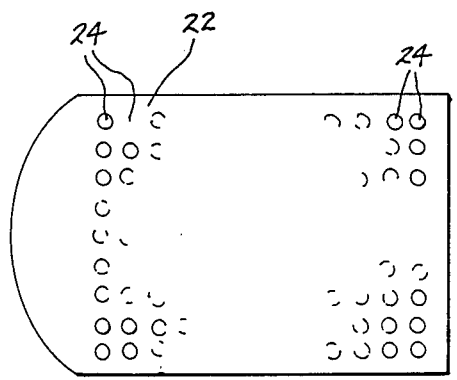

Silver/silver chloride layer 24 may comprise continuous layer, as shown in FIG. 2. Or, the silver/silver chloride layer 24 may be applied in a pattern or discontinuous layer, as shown in FIGS. 4 and 5, thereby to reduce the cost of the silver/silver chloride layer. For example, as shown in FIG. 4, layer 24 may be applied to carbon layer 22 in a grid like pattern. Carbon layer 22 may be applied in the manner shown in FIG. 2 or in a pattern similar to layer 24 with appropriate connection provided for lead clip 18. Or, as shown in FIG. 5, silver/silver chloride layer 24 may take the form of a plurality of dots applied to carbon layer 22. With the embodiment of the invention shown in FIGS. 4 and 5, the amount of carbon or thickness of carbon layer 22 may be increased as the silver/silver chloride is reduced to maintain the electrical properties of electrode 10.

Figure 6:
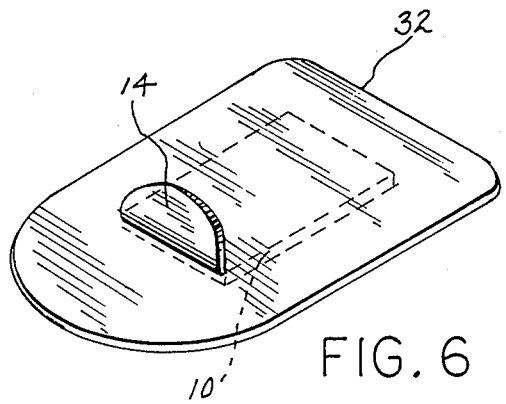
FIG. 6 is a perspective view of a modification of the electrode of the present invention.

While adhesive layer 26 is capable of retaining electrode 10 on the skin of the patient in many applications, it may be desirable to provide additional adhesion for electrode 10 in other applications. Typical of such other applications is a stress electrode for electrocardiographic purposes in which the electrode must remain attached to the patient during exercise. As shown in FIG. 6, a cover 32 having adhesive on the lower side thereof can be applied over the electrode to increase the adhesive area of the electrode. Layer 32 may comprise foam, plastic, cloth or other suitable material. Connection tab 14 may extend through layer 32.

Figure 7:
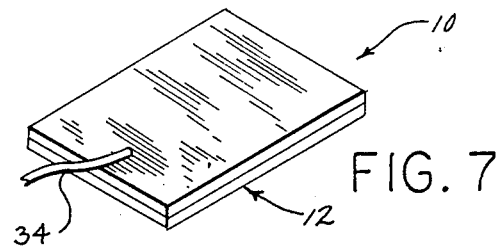
FIG. 7 is a perspective view of a further modification of the electrode of the present invention.

Also, while electrode 10 is shown and described as using tab 14 for connection purposes, it will be appreciated that other connection means may be provided. For example, as shown in FIG. 7, electrode 10 may include lead wire 34 connected to layer 22 and/or layer 24. Lead wire 34 is connected to appropriate instrumentation.

While electrode 10 of the present invention has been described, in exemplary fashion as an electrocardiographic electrode, it will be appreciated that it may be utilized in conjunction with other biopotential measurements, such as electroencephalography, or in other bioelectrical applications.

Various modes of carrying out the invention are contemplated as being within the scope of the following claims particularly pointing out and distinctly claiming the subject matter which is regarded as the invention.

We claim:

1. A disposable, biopotential electrode structure providing improved electrical properties and comprising:
    a flat, sheet-like flexible base having first and second orthogonal dimensions lying in the plane of, said base, said first orthogonal dimension terminating at a pair of ends, said base having defined thereon an electrode portion for receiving biopotential signals and a connector portion for supplying the signals externally of said electrode structure, said electrode portion and connector portion lying in a generally side by side contiguous relationship on said base along said first orthogonal dimension with said portions at opposite ends of said first orthogonal dimension, said electrode portion having substantially the same dimension as said base along said second orthogonal dimension;
    electrically conductive carbon material associated with said base in quantities sufficient to render said electrode portion electrically conducting, said carbon material being associated at least coterminously with said electrode portion;
    a layer of silver/silver chloride having dimensions at least coterminous with those of said electrode portion, said layer being electrically coupled to said carbon material, said carbon material associated with said base serving to lessen the amount of silver/silver chloride in said layer while enabling the improved electrical properties to be provided in said electrode structure;
    at least one of said electrically conductive carbon material and silver/silver chloride layer extending into said connector portion; and
    and an ionically conductive adhesive lying over said silver/silver chloride layer, said adhesive being coextensive with said electrode portion.

2. The electrode structure according to claim 1 wherein said carbon material is contained in a layer intermediate said base and said silver/silver chloride layer.

3. The electrode structure according to claim 2 wherein said carbon material is contained in a binder applied to said base sheet.

4. The electrode structure according to claim 2 wherein said carbon material is contained in a carrier film applied to said base sheet.

5. The electrode structure according to claim 1 wherein said carbon material comprises at least one of carbon and graphite.

6. The electrode structure according to claim 1 wherein said layer of silver/silver chloride comprises a continuous layer.

7. The electrode structure according to claim 6 wherein said carbon material is associated with at least all of said electrode portion.

8. The electrode structure according to claim 1 wherein said layer of silver/silver chloride comprises a discontinuous layer.

9. The electrode structure according to claim 8 wherein said carbon material is associated with at least all of said electrode portion.

10. The electrode structure according to claim 8 where in said carbon material is associated with at least a portion of said electrode portion of said base.

11. The electrode structure according to claim 1 wherein said carbon material is associated with at least all of said electrode portion.

12. The electrode structure according to claim 1 wherein said carbon material is associated with at least a portion of said electrode portion of said base.

13. The electrode structure according to claim 1 wherein said base comprises a plastic material.

14. The electrode structure according to claim 1 wherein said electrode structure includes adhesive means applied to said base and extending beyond said base for providing additional adhesive area to said electrode structure.

15. A disposable, electrodcardiographic electrode structure providing improved electrical properties comprising:

a flat, sheet-like, flexible base having first and second orthogonal dimensions lying in the plane of said flat sheet-like base, said first dimension terminating at a pair of ends, said base having defined thereon an electrode portion for receiving electrocardiographic signals and a connector portion for supplying said signals externally of said electrode structure, said electrode portion and connector portion lying in a generally side by side contiguous relationship on said base along said first orthogonal dimension with said portions at opposite ends of said first orthogonal dimension, said electrode portion having substantially the same dimension as said base sheet along said second orthogonal dimension;

a layer of electrically conductive carbon material on said base having dimensions at least coterminous with those of said electrode portion, said carbon material being present in quantities sufficient to render said electrode portion electrically conductive;

a layer of silver/silver chloride on said carbon material layer; said silver/silver chloride layer having dimensions at least coterminous with those of said electrode portion, said carbon material serving to lessen the amount of silver/silver chloride in said silver/silver chloride layer while enabling the improved electrical properties to be provided in said electrode structure;

at least one of said carbon material layer and silver/silver chloride layer extending into said connector portion; and an ionically conductive adhesive on said silver/silver chloride layer coextensive with said electrode portion.

* * * * *